US009439916B2

(12) United States Patent
Skulachev et al.

(10) Patent No.: US 9,439,916 B2
(45) Date of Patent: *Sep. 13, 2016

(54) COMPOSITION FOR DECELERATING THE AGING IN THE ORGANISM AND FOR EXTENDING THE LIFE TIME THEREOF AND THE USE OF SAID COMPOSITION

(75) Inventors: Maxim V. Skulachev, Moscow (RU); Vladimir P. Skulachev, Moscow (RU)

(73) Assignee: MITOTECH SA, Luxembourg (LU)

( * ) Notice: Subject to any disclaimer, the term of this patent is extended or adjusted under 35 U.S.C. 154(b) by 511 days.

This patent is subject to a terminal disclaimer.

(21) Appl. No.: 12/595,648

(22) PCT Filed: Apr. 11, 2007

(86) PCT No.: PCT/RU2007/000171
§ 371 (c)(1),
(2), (4) Date: Mar. 29, 2010

(87) PCT Pub. No.: WO2008/127138
PCT Pub. Date: Oct. 23, 2008

(65) Prior Publication Data
US 2010/0234326 A1    Sep. 16, 2010

(51) Int. Cl.
*A61K 31/66*    (2006.01)
*A61K 31/122*   (2006.01)

(52) U.S. Cl.
CPC .................... *A61K 31/66* (2013.01)

(58) Field of Classification Search
CPC ............................ A61K 31/66; A61K 31/122
See application file for complete search history.

(56) References Cited

U.S. PATENT DOCUMENTS

| 5,538,974 | A | 7/1996 | Ogawa et al. | |
| 6,331,532 | B1 | 12/2001 | Murphy et al. | |
| 7,109,189 | B2 | 9/2006 | Murphy et al. | |
| 2002/0048798 | A1* | 4/2002 | Avery et al. ................ | 435/183 |
| 2005/0065099 | A1 | 3/2005 | Walkinshaw et al. | |
| 2007/0259908 | A1 | 11/2007 | Fujii et al. | |
| 2007/0270381 | A1 | 11/2007 | Murphy et al. | |
| 2008/0275005 | A1 | 11/2008 | Murphy et al. | |

FOREIGN PATENT DOCUMENTS

| EP | 1047701 | B1 | 5/2005 |
| EP | 1534720 | A1 | 6/2005 |
| EP | 1321138 | B1 | 4/2006 |
| RU | 2318500 | C2 | 3/2008 |
| WO | 9926582 | | 6/1999 |
| WO | 2004/014927 | A1 | 2/2004 |
| WO | 2006/005759 | A2 | 1/2006 |
| WO | 2007/046729 | A1 | 4/2007 |
| WO | 2008/048134 | A1 | 4/2008 |
| WO | 2009/005386 | A1 | 1/2009 |
| WO | 2009/158348 | A1 | 12/2009 |

OTHER PUBLICATIONS

Grey, A. "The foreseeability of real anti-aging medicine: focusing the debate" Experimental Gerontoogy, 2003, vol. 38, pp. 927-934.*
Horovitz et al. "Cancer of the Colon" Dis Colon Rectum, 1980, vol. 23, pp. 76-79.*
Klein et al. "The Relationship of Age-Related Maculopathy, Cataract, and Glaucoma to Visual Acuity" invest Ophthalmol Vis Sci, 1995, vol. 36, pp. 182-191.*
Olshansky et al. "Position Statement on Human Aging" Sci Aging Knowl Environ, Jun. 2002, vol. 2002, issue 24, p. pe9, printed pp. 1-5.*
Rall et al. "Urinary 8-hydroxy-2'-deoxyguanosine (8-OHdG) as a marker of oxidative stress in rheumatoid arthritis and aging: Effect of progressive resistance training" J. Nutr. Biochem, 2000, vol. 11, pp. 581-584.*
Stella et al. "Prodrugs: the control of drug delivery via bioreversible chemical modification", Drug Delivery Systems Characteristics and Biomedical Applications, 1980, Oxford University Press, pp. 112-176.*
Morissette et al. "High-throughput crystallization: polymorphs, salts, co-crystals and solvates of pharmaceutical solids" Advanced Drug Delivery Reviews, 2004, vol. 56, pp. 275-300.*
J. G. G Cannon Chapter Nineteen in Burger's Medicinal Chemistry and Drug Discovery, Fifth Edition, vol. I: Principles and Practice, Wiley-Interscience 1995, pp. 783-802, 784.*
Sheridan, R.P. "The Most Common Chemical Replacements in Drug-Like Compounds" J. Chem.Inf.Comput.Sci., 2002, vol. 42, pp. 103-108.*
Durany et al. "Investigatins on oxidtive stress and therapeutical implications in dementia" Eur. Arch. Psychiatry. Clin. Neurosci., 1999, vol. 249, Suppl. 3, pp. III/68-III/73.*
Basu et al. "Association between Oxidative Stress and Bone Mineral Density" Biochemical and Biophysical Communications, Oct. 2001, vol. 288, issue 1, pp. 275-279.*
Dominguez LJ, "Ageing, lifestyle modifications, and cardiovascular disease in developing countries," J. Nutr. Health Aging, 10(2):143-149 (2006).
Holloszy, "Longevity of exercising male rats: effect of an antioxidant supplemented diet," Mechanisms of Ageing and Development, 100:211-219 (1998).
Liu et al., "Age-associated changes in superoxide dismutase activity, thiobarbituric acid reactivity and reduced glutathione level in the brain and liver in senescence accelerated mice (SAM): a comparison with ddY mice," Mech. Aging Dev., 71:23-30 (1993).

(Continued)

*Primary Examiner* — Kendra D Carter
(74) *Attorney, Agent, or Firm* — Wayne A. Keown; Verrill Dana LLP

(57) ABSTRACT

The invention relates to pharmacology, medicine and gerontology, in particular to a class of chemical structures (1) which can be used in compositions, in the form of geroprotectors, for extending the life time, decelerating, stopping or for reversing the process of the entirety of the organism's dysfunctions causing the mammal ageing and for preventing and treating particular senile diseases.

7 Claims, 6 Drawing Sheets

(56) References Cited

OTHER PUBLICATIONS

Longo et al., "Programmed and altruistic ageing," Nature Review Genetics, 6:866-872 (2005).
Mecocci et al., "Plasma antioxidants and longevity: a study on healthy centenarians," Free Radical Biology and Medicine, 28(8):1243-1248 (2000).
Orr et al., "Effects of overexpression of copper-zinc and manganese superoxide dismutases, catalase, and thioredoxin reductase genes on longevity in Drosophila melanogaster," J. Biol. Chem., 278(29):26418-26422 (2003).
Reliene et al., "Antioxidants suppress lymphoma and increase longevity in atm-deficient mice," The Journal of Nutrition, 137:229S-232S (2007).
Sidorova et al., "Transcriptional activation of cytochrome P450 1A1 with alpha-tocopherol," Bull Exp. Bio. Med., 138 (3):233-236 (2004).
Skulachev VP, "Aging and the programmed death phenomena," Topics in Current Genetics, vol. 3, Nystrom and Osiewacz, Eds., Model systems in Ageing, Springer-Verlag Berlin Heidelberg 191-283 (2003).
International Search Report and Written Opinion of the International Searching Authority, PCT/RU2007/000171, Dec. 20, 2007.
Adlam et al. (2005) "Targeting an antioxidant to mitochondria decreases cardiac ischemia-reperfusion injury," FASEB J., 19:1088-1095.
Agapova et al. (2008) "Mitochondria-Targeted Plastoquinone Derivatives as Tools to Interrupt Execution of the Aging Program. 3. Inhibitory Effect of SkQ1 on Tumor Development From p53-Deficient Cells," Biochem. (Mosc)., 73 (12):1300-1316 (+ 3 fig. pages).
Anisimov (2007) "Molecular and Physiological Mechanisms of Aging," Antioksidanty, Nov. 27, 2007, [on line] http://imquest.alfaspace.net/BOOK/MFMA/mfma_3_92.htm?embedded=yes translated from Russian to English.
Antonenko et al. (2008) "Mitochondria-Targeted Plastoquinone Derivatives as Tools to Interrupt Execution of the Aging Program. 1. Cationic Plastoquinone Derivatives: Sythesis and in vitro Studies," Biochemistry, 73(12)1273-1287.
Antonenko et al. (2008) "Protective effects of mitochondria-targeted antioxidant SkQ in aqueous and lipid membrane environments," J. Membr. Biol., 222:141-149.
Becker (2004) "New concepts in reactive oxygen species and cardiovascular reperfusion physiology" Cardiovascular Research, 61:461-470.
Berge et al. (1977) "Pharmaceutical Salts," J. Pharma. Sci., 66(1):1-19.
Blaikie et al. (2006) "Targeting Dinitrophenol to Mitochondria: Limitations to the Development of a Self-limiting Mitochondrial Protonophore," Biosci. Rep, 26:231-243.
Brand et al. (1992) "The mechanism of the increase in mitochondrial proton permeability induced by thyroid hormones," Eur. J. Biochem. 206:775-781.
Doughan et al. (2007) "Original Research Communication: Mitochondrial Redox Cycling of Mitoquinone Leads to superoxide Production and Cellular Apoptosis," Antioxid. Redox Signal., 9(11):1825-1836.
Kasahara, et al. (2005) "Manganese Superoxide Dismutase protects against oxidation-induced apoptosis in mouse retinal pigment epithelium: implications for age-related macular degeneration," Author Manuscript, NIH Public Access PMC Nov. 1, 2005: 1-18, Invest. Ophthalmol. Vis. Sci., 46(9):3426-3434.
Green et al. (2004) "Prevention of Mitochondrial Oxidative Damage as a Therapeutic Strategy in Diabetes," Diabetes, 53(1):S110-S118.
Hansford et al. (1997) "Dependence of H2O2 formation by rat heart mitochondria on substrate availability and donor age," J. Bioenerg. Biomem. 29(1):89-95.

Havens et al. (2006) "Regulation of Late G1/S Phase Transition and APCCdh1 by Reactive Oxygen Species," Mol. Cell. Biol., 26(12):4701-4711.
Neroev et al. (2008) Mitochondria-Targeted Plastoquinone Derivatives as Tools to Interrupt Execution of the Aging Program. 4. Age-Related Eye Disease. SkQ1 Returns Vision to Blind Animals, Biochemistry (Mosc.), 73 (12):1317-1328.
King et al. (2004) "Mitochondria-derived reactive oxygen species mediate blue light-induced death of retinal pigment epithelial cells," Photochem. and Photobiol., 79(5):470-475.
Kirschner et al. (1994) "Role of iron and oxygen-derived free radicals in ischemia-reperfusion injury" J. Am. Coll. Surg., 179:103-117.
Li et al. (2000) "Skeletal muscle respiratory uncoupling prevents diet-induced obesity and insulin resistance in mice," Nat. Med. 6(10):1115-1120.
Sheu et al. (2006) "Targeting antioxidants to mitochondria: a new therapeutic direction," Biochimica et Biophysica Acta, 1762:256-265.
Popova et al. (2006) "MitoQ induced miofibroblast differentiation of human fibroblasts," Biochimica et Biophysica Acta, S:433-434.
Lou et al. (2007) "Mitochondrial Uncouplers With an Extraordinary Dynamic Range," Biochem. J., 407:129-140.
Reddy (2006) "Mitochondrial oxidative damage in aging and Alzheimer's disease: implications for mitochondrially targeted antioxidant therapeutics," J. Biomedicine and Biotech., Art.ID 31372:1-13.
Skulachev (2005) "Critical Review: How to Clean the Dirtiest Place in the Cell: Cationic Antioxidants as Intramitochondrial Ros Scavengers," IUBMB Life, 57(4/5):305-310.
Riess et al. (2004) "Reduced reactive O2 species formation and preserved mitochondrial NADH and [Ca2+] levels during short-term 17°C ischemia in intact hearts," Cardiovascular Research, 61:580-590.
Papp et al. (1999) "Glutathione status in retinopathy of prematurity," Free Radic. Biol. & Med., 27(7-8):738-743.
Petrosillo et al. (2005) "Mitochondrial dysfunction associated with cardiac ischemia/reperfusion can be attenuated by oxygen tension control. Role of oxygen-free radicals and cardiolipin," Biochimica et Biophysica Acta, 1710:78-86.
Petrosillo et al. (2006) "Protective effect of melatonin against mitochondrial dysfunction associated with cardiac ischemia-reperfusion: role of cardiolipin," FASEB J., 20:269-276.
Skulachev (2007) "A Biochemical Approach to the Problem of Aging: 'Megaproject' on Membrane-Penetrating Ions. The First Results and Prospects," Biochem. (Moscow), 72(12):1385-1396.
Popova et al. (2010) "Scavenging of Reactive Oxygen Species in Mitochondria Induces Myofibroblast Differentiation," Antiox. & Redox. Signal., 13(9):1297-1307.
Pozniakovsky et al. (2005) "Role of mitochondria in the pheromone- and amiodarone-induced programmed death of yeast," J. Cell Biol., 168(2):257-69.
Sundaresan et al. (1995) "Requirement for Generation of H2O2 for Platelet-Derived Growth Factor Signal Transduction," Science, 270:296-299.
Yildirim et al. (2005) "Role of oxidative stress enzymes in open-angle glaucoma," Eye, 19:580-583.
Zweier et al. (1987) "Direct measurement of free radical generation following reperfusion of ischemic myocardium," PNAS USA, 84:1404-1407.
Starkov et al. (1997) "6-ketocholestanol is a recoupler for mitochondria, chromatophores and cytochrome oxidase proteoliposomes," Biochim. Biophys. Acta. 1318:159-172.
Tompkins et al. (2006) "Mitochondrial dysfunction in cardiac ischemia-reperfusion injury: ROS from complex I, without inhibition," Biochim. Biophys. Acta. 1762:223-231.
Bakeeva et al. (2008) "Mitochondria-targeted plastoquinone derivatives as tools to interrupt execution of the aging program. 2. Treatment of some ROS- and Age-related diseases (heart arrhythmia, heart infarctions, kidney ischemia, and stroke)," Biochemistry (Moscow), 73(12):1288-1299 and 1 figure.

(56) References Cited

OTHER PUBLICATIONS

Clem et al. (2008) "Small-molecule inhibition of 6-phosphofructo-2-kinase activity suppresses glycolytic flux and tumor growth," Mol. Canc. Ther. 7(1):110-120.
Goldstein (2002) "Reactive oxygen species as essential components of ambient air," Biochemistry (Mosc.) 67:161-170.
Green (1974) "The electromechanochemical model for energy coupling in mitochondria," Biochimica et Biophysica Acta, 346:27-78.
Kirste et al. (1995) "Continuous-wave electron spin resonance studies of porphyrin and porphyrin-quinone triplet states," J. Chem. Soc. Perkin Trans. 2:2147-2152.
Murphy et al. (2007) Targeting antioxidants to mitochondria by conjugation to lipophilic cations. Annu. Rev. Pharmacol. Toxicol., 47:629-656.
Skulachev et al. (2009) "An attempt to prevent senescence: a mitochondrial approach," Biochimica et Biophysica Acta., 1787:437-461.
Smith et al. (2008) "Mitochondria-targeted antioxidants in the treatment of disease,"Ann. N.Y. Acad. Sci., 1147:105-111.
Snow et al. (2010) "A double-blind, placebo-controlled study to assess the mitochondria-targeted antioxidant MitoQ as a disease-modifying therapy in Parkinson's disease," Mov. Disord. 25(11):1670-1674.
Stefanova et al. (2010) "Behavioral effects induced by mitochondria-targeted antioxidant SkQ1 in Wistar and senescence-accelerated OXYS rats," J. Alzheimer's Dis. 21:479-491.
Triet et al. (1993) "Anxiogenic stimuli in the elevated plus-maze," Pharmacol. Biochem. & Behav. 44:463-469.
Plotnikov et al. (2008) "Interrelations of Mitochondrial Fragmentation and Cell Death Under Ischemia/Reoxygenation and UV-Irradiation: Protective Effects of SkQ1, Lithium Ions and Insulin," FEBS Letters, 582:3117-3124.
Plotnikov et al. (2010) "New-generation Skulachev ions exhibiting nephroprotective and neuroprotective properties." Biochemistry (Mosc.), 75(2):145-150.
Skulachev et al. (2005) "Aging as mitochondria-mediated atavistic program. Can aging be switched off?" Ann. NY Acad. Sci., 1057:145-164.
Tauskela (2007) "MitoQ—a mitochondria-targeted antioxidant," IDrugs, 10:399-412.
International Search Report and Written Opinion, PCT/RU2009/000621, dated Aug. 12, 2010 (12 pages).
PCT International Search Report and Written Opinion of the International Searching Authority for PCT Application No. PCT/RU2006/000546, mailed Jul. 5, 2007, 14 pages.
PCT International Search Report mailed Nov. 1, 2007 and International Preliminary Report on Patentability issued Aug. 4, 2009 for PCT Application No. PCT/RU2007/000043, 9 pages.
International Search Report and Written Opinion of the International Searching Authority, PCT/RU2009/000295, Feb. 25, 2010, 7 pages.
International Search Report and Written Opinion, PCT/RU2006/000547, dated Jul. 15, 2007 (7 pages).
International Search Report and Written Opinion of the International Searching Authority, PCT/RU2007/000355, Mar. 27, 2008 (10 pages).
International Search Report and Written Opinion, PCT/RU2006/000394, dated Nov. 2, 2006 (6 pages).
International Search Report dated Dec. 20, 2007 and International Preliminary Report on Patentability dated Nov. 10, 2009, PCT/RU2007/000171 (16 pages).
International Search Report, PCT/RU2008/000706, Aug. 13, 2009 (3 pages).
International Search Report and Written Opinion of the International Searching Authority, PCT/RU2007/000044, Nov. 1, 2007, 9 pages.
PubChem compound CID 388445; Mar. 26, 2005 [retrieved from http://pubchem.ncbi.nlm.nih.gov/summary/summary.cgi?cid=38845&loc=ec_rcs on Jul. 31, 2012] whole doc (4 pages).
International Search Report and Written Opinion of the International Searching Authority, PCT/US12/40711, Aug. 20, 2012 (9 pages).

\* cited by examiner

COMPOSITION FOR DECELERATING THE AGING IN THE ORGANISM AND FOR EXTENDING THE LIFE TIME THEREOF AND THE USE OF SAID COMPOSITION

FIELD OF THE INVENTION

The invention relates to pharmacology, medicine and gerontology, in particular to a class of chemical structures (I) which can be used in the composition of medicines (preparations) in the fight against various senile diseases, decelerating the ageing, extending the life span of animals including humans.

BACKGROUND OF THE INVENTION

Nowadays the ageing problem is no longer limited to biological and medical aspects and begins to reach the level of the universal economic problem. In developed countries elderly people are already quantitatively prevail over youth, and the next 25 years the proportion of elderly people in the world will increase by 80% and the proportion of working-age population will decrease accordingly. (Dominguez L. J. Ageing, lifestyle modifications, and cardiovascular disease in developing countries. //J. Nutr. Health Aging, 2006, 10, 2, 143-9). It is obvious that such demographic changes will affect all spheres of life. Mankind will face an acute shortage of resources needed to address the ageing population problems and development issues in general, and therefore the problem of decelerating the human ageing and preventing the development of senile diseases is becoming increasingly important.

Ageing is a comprehensive and complex process accompanied by dysfunctions in the functioning of critical systems of regulation at the level of the whole organism, at the cellular and molecular levels. Such changes can be observed in various systems of the organism, such as the nervous system (decrease in brain mass, the size and density of neurons, the fall of the bioelectric activity of nerve cells, changes in behavior and learning ability, lipofuscin deposition), the digestive system (e.g., reduction of secretory activity of the digestive organs), the secretory system (reduction of basic renal function), the cardiovascular system (reduction of contractile capacity of the myocardium, increase in systolic blood pressure, slowing of heart rhythmic activity). Also, visual acuity and accommodative power of the eye are reduced, degenerative changes in the retina and cornea are accelerated. There are a slowdown and decrease in protein biosynthesis, increased fat content in various tissues and blood, change in lipid fractions ratio, increase in the frequency of lower tolerance towards carbohydrates and insulin supply to the organism. Degenerative processes in the skeleton (osteoporosis) are accelerated.

It is generally accepted that the slow poisoning of the organism by toxic oxygen species (ROS) plays a key role in the processes of ageing (V. P. Skulachev (2003) Aging and the programmed death phenomena. In: Topics in Current Genetics, Vol. 3 (T. Nystrom and H. D. Osiewacz, Eds.) Model systems in ageing. Springer-Verlag Berlin Heidelberg, pp. 191-238; V. P. Skulachev (2005) Aging as an atavistic program that we can attempt to cancel. Herald of the Russian Academy of Sciences (in Russian) 75, 831-843). High levels of antioxidants (such as vitamins A and E) in the organism are known to be characteristic of long-livers (Mecocci et al. Plasma antioxidants and longevity: a study on healthy centenarians //Free Radical Biology and Medicine, 2000, 28, 8, 1243-48); on the contrary, genetically determined dysfunctions in the antioxidant systems of the organism lead to accelerated ageing and reduction of the average life expectancy (Liu, J. & Mori A. Age-associated changes in superoxide dismutase activity, thiobarbituric acid reactivity and reduced glutathione level in the brain and liver in senescence accelerated mice (SAM): A comparison with ddY mice. //Mech. Aging Dev., 1993, 71, 23-30). Attempts to fight against senile diseases, and, ultimately, postpone ageing and death of the organism have been made repeatedly. The approaches used so far to strengthen the antioxidant protection have a positive effect mainly on various ageing-associated diseases, however both average life expectancy and maximum life span usually does not increase (Holloszy J. O. Longevity of exercising male rats: effect of an antioxidant supplemented diet. //Mechanisms of Ageing and Development, 1998, 100, 211-219; Orr, W. C. et al. Effects of overexpression of copper-zinc and manganese superoxide dismutases, catalase, and thioredoxin reductase genes on longevity in *Drosophila melanogaster*. //J Biol Chem., 200, 3 278 (29), 26418-26422). The data on anti-oxidant-induced extension of life span in the organisms with pathologically accelerated ageing, relative to normal members of their species, are the exception. For example, antioxidants can increase the average life expectancy of mice in a state of permanent oxidative stress due to dysfunctions in the ATM gene (Reliene R. & Schiestl R. Antioxidants Suppress Lymphoma and Increase Longevity in Atm-Deficient Mice //The Journal of Nutrition, 2007, 37, 229S-232S). According to the theory implying that ageing is part of the program(s) of the individual organism's development, low efficiency of the antioxidants used so far can be accounted for by organism's intention to fulfill the ageing program encoded in its genome despite our attempts to stop it. Indeed, the introduction of large doses of vitamin E appeared to induce the cytochrome P450 enzyme in liver microsomes which removes the excess antioxidant (Y. A. Sidorova, A. Y. Grishanova, V. V. Lyakhovich (2004). Transcriptional activation of cytochrome P450 1A1 with alpha-tocopherol. Bull Exp Biol Med., 138(3), 233-6.). Apart from the susceptibility to antioxidant-scavenging enzymes in the organism, traditional antioxidants have a disadvantage that they are uniformly distributed throughout the cell volume, rather than accumulate in the mitochondria responsible for generating the bulk of ROS in the organism.

Many known remedies increase the average life expectancy (ALE) of animals and humans. However the maximum life span (MLS) is not increased which implies that these remedies are aimed at correcting the pathological consequences of ageing, rather than the fundamental processes of ageing. Thus, mankind has almost exhausted the possibilities of extending the life span by traditional medicines, and in the first place there is a problem of developing means and methods of a radical impact on the ageing process. In this case, the term "the fight against ageing" implies decelerating, stopping or reversing the process of the entirety of the organism's dysfunctions causing the ageing, extending the life time, prevention or correction of dysfunctions that accompany the ageing process, in order to increase the length of productive life, and postpone these senile dysfunctions to a later date (or even cancel them).

The assumption of the possible effect of increasing life span and decelerating ageing induced by described compounds of structure (1) was also made in the patent application of the author of the given invention registered under the number RU 2005132217 dated Oct. 19, 2005. However, the experimental examples shown in the given patent application are only vaguely related to both the problem of extending the life time in general and specific senile diseases, and do not allow to state the usefulness of compounds of structure (1) in the fight against ageing as such.

DESCRIPTION OF THE INVENTION

The present invention suggests not only a theoretical possibility of the fight against ageing, but also a specific method based on the use of a set of compounds specifically addressed to the mitochondria by virtue of their positive charge. This charge is shielded by hydrophobic substituents that endows the compounds with the ability to penetrate through biological membranes without the aid of any carriers under the influence of electrical potential difference that is always available in the mitochondrion (the sign "minus"—inside the mitochondrion). The invention provides not only a potential ability for the fight against ageing with the use of said compounds, but also specific compositions, modes and procedures of their application for the fight against ageing.

One aspect of the present invention is a new application of a pharmaceutical composition of cationic antioxidants to produce medicinal preparations that are intended for the prevention and treatment of various pathologies of ageing and extending the productive life time. Said composition comprises compounds that include targeting moiety, linker group and antioxidant, and the general chemical structure of these compounds can be described by the following structure (I):

wherein A is effector moiety—antioxidant

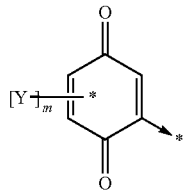

and/or reduced form thereof wherein m is an integer from 1 to 3; each Y is independently selected from the group consisting of: lower alkyl, lower alkoxy; or two adjacent Y groups, together with carbon atoms to which they are attached, form a following structure:

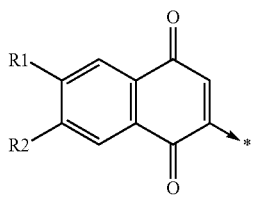

and/or reduced form thereof wherein R1 and R2 may be the same or different and are each independently lower alkyl or lower alkoxy;

L—linker group, comprising:
a) straight or branched hydrocarbon chain which can be optionally substituted by one or more substituents and optionally contains one or more double or triple bonds;
b) natural isoprene chain;
n is integer from 1 to 20;
B—targeting group comprising Skulachev-ion Sk:

$Sk^+Z^-$ where Sk—lipophilic cation, Z—pharmacologically acceptable anion; with proviso that in compound of structure (I) A is not ubiquinone (e.g., 2-methyl-4,5-dimethoxy-3,6-dioxo-1,4-cyclohexadienyl) or tocopherol or mimetic of superoxide dismutase or ebselen; while L—divalent decyl or divalent pentyl or divalent propyl radical; and while B is triphenylphosphonium cation; or solvates, isomers and prodrugs; and pharmaceutically acceptable carrier thereof.

Another aspect of the present invention is the use of a pharmaceutical composition for manufacturing medicinal preparations that are intended for extending the life time of humans and animals, as well as for prevention and treatment of senile diseases, such as retinal dystrophy, cataract, uveitis, glaucoma, cardiac infarction, renal infarction, stroke, diabetes, trophic ulcers, mental disorders, anemia, osteoporosis, cancer, etc.

One more aspect of the present invention is a pattern of use (treatment course) suggesting the use of high doses of a preparation comprising a compound of structure (I), in the treatment of older patients, as well as a gradual increase in dosage preparation comprising a compound of structure (I), with increasing age of individual patient. Such procedure is intended to compensate for age-related reduction of natural antioxidant protection of the organism with ageing. Acceptable doses for oral administration are from 1 nanogram to 100 microgram per kg of patient body weight, 60 nanogram per kg of body weight of patients aged from birth to 10 years is more preferable; from 1 nanogram to 500 microgram per kg of patient body weight, 600 nanogram per kg of body weight of patients aged 10 to 25 years is more preferable; from 5 nanogram to 1000 microgram per kg of patient body weight, 3 microgram per kg of body weight of patients aged 25 to 40 years is more preferable; from 10 nanogram to 10000 microgram per kg of patient body weight, 30 microgram per kg of body weight of patients aged 40 years and older is more preferable.

In the present invention, the wording "extending the life span" means extending the life span that can be achieved by decelerating the ageing, decelerating or reversing the age-dependent changes in the organism. Without wishing to be bound by any theory, solely to illustrate the possibility of implementing the present invention, a possible theoretical justification that mitochondria-addressed compounds of structure (I) may affect the ageing process is given below.

The said justification is based on the theory of programmed death of the organism (phenoptosis) (V. D. Longo, J. Mitteldorf and V. P. Skulachev (2005) Programmed and altruistic ageing. Nature Review Genetics 6, 866-872). According to this theory, in a large number of cases, the reason of "age-induced" death of the organism is not because the organism "exhausted its own resource", but is due to the action of the program encoded in this organism that specifically and actively limits its life span.

In nature, many cases of programmed death of the organism have been described, and for different species this program can be implemented in different ways. However, the scientific data available (see Background of the invention) suggest that ROS formed in the mitochondria play an important role in implementing this program. Hence, compounds of structure (I) may affect the said program.

Application of pharmaceutical compositions relating to the present invention can be both somatic and local. Procedures of administration comprise enteral, such as oral, sublingual and rectal; local, such as transdermal, intradermal and oculodermal; and parenteral. Suitable parenteral procedures of administration comprise injections, for example, intravenous, intramuscular, subdermal, intraperitoneal, intra-arterial, and other injections, and non-injecting practices, such as vaginal or nasal. Preferably, compounds and pharmaceutical compositions related to the present invention, are for parenteral or oral administration. In particular, administration can be given in form of intravenous injections or tablets, granules, capsules or other pressed or compressed form.

When a compound of structure (I) is administered as a pharmaceutical composition, a compound of structure (I) should be mixed according to formula with a suitable amount of pharmacologically acceptable solvent or carrier so that to have the appropriate form for administration to a patient. The term "solvent" relates to diluent, auxiliary medicinal substance, filler or carrier which is mixed with a compound of structure (I) for administration to a patient. Liquors like water, and oils including petrolic, animal, vegetative and synthetic, such as peanut oil, soybean oil, mineral oil and other similar oils can be used as said pharmacological carriers. Normal saline solution, acacia pitch, gelatin, starch, talc, keratin, colloid silver, urea etc can serve as said pharmacological solvents.

Said composition can also include auxiliary substances, stabilizers, thickeners, lubricant and coloring agents.

Compounds and compositions related to the present invention can be administered in form of capsules, tablets, pills, pillets, granules, syrups, elixirs, solutions, suspensions, emulsions, suppositories or retarded release substances, or in any other form suitable for administration to a patient. One aspect of the present invention is application of compounds of structure (I) and compositions in form of solutions for oral and parenteral administration.

Therapeutically justified amount of a compound of structure (I) required for treatment of a specific disease or symptom, depends on the nature of disease or symptom and a procedure of administration and should be determined at consultation with a physician in charge. Acceptable doses for oral administration are from 0.025 to 120000 microgram per kg of patient body weight, 1.5 microgram per kg of patient body weight is more preferable, and 3 microgram per kg of patient body weight is the most preferable. Acceptable doses for intravenous administration are from 0.001 to 10000 microgram per kg of patient body weight, 0.01 microgram per kg of patient body weight is more preferable, and 0.1 microgram per kg of patient body weight is the most preferable.

Examples of Acceptable Pharmaceutical Compositions for Oral Administration:
Pharmaceutical Composition—1—Gelatin Capsules:

| Ingredient | Amount (mg/capsule) |
| --- | --- |
| Compound of structure (I) | 0.0015-1000 |
| Starch | 0-650 |
| Starch powder | 0-650 |
| Liquid silicone | 0-15 |

Pharmaceutical Composition—2—Tablets:

| Ingredient | Amount (mg/capsule) |
| --- | --- |
| Compound of structure (I) | 0.0015-1000 |
| Microcrystalline cellulose | 200-650 |
| Silicon dioxide powder | 10-650 |
| Stearic acid | 5-15 |

Pharmaceutical Composition—3—Tablets:

| Ingredient | Amount (mg/capsule) |
| --- | --- |
| Compound of structure (I) | 0.0015-1000 |
| Starch | 45 |
| Microcrystalline cellulose | 35 |
| Polyvinylpyrrolidone (10% aqueous solution) | 4 |
| Carboxymethylcellulose, sodium salt | 4.5 |
| Talc | 1 |
| Magnesium stearate | 0.5 |

Pharmaceutical Composition—4—Suspensions:

| Ingredient | Amount (mg/5 ml) |
| --- | --- |
| Compound of structure (I) | 0.0015-1000 |
| Syrup | 1.25 |
| Benzoic acid solution | 0.10 |
| Carboxymethylcellulose, sodium salt | 50 |
| Flavoring | By necessity |
| Coloring | By necessity |
| Distilled water | Up to 5 ml |

An Example of Acceptable Pharmaceutical Composition for Administration in the Form of Aerosol:

| Ingredient | Amount (weight percent) |
| --- | --- |
| Compound of structure (I) | 0.0025 |
| Ethanol | 25.75 |
| Difluorochloromethane | 70 |

An Example of Acceptable Pharmaceutical Composition for Administration in the Form of Suppositories:

| Ingredient | Amount (mg/suppository) |
| --- | --- |
| Compound of structure (I) | 1 |
| Glycerides of saturated fatty acids | 2000 |

An Example of Acceptable Pharmaceutical Composition in the Form of Solution for Intravenous Administration (pH 6.51):

| Ingredient | Amount |
| --- | --- |
| Compound of structure (I) | 5 mg |
| Isotonic solution | 1000 ml |

The following non-limiting Examples illustrate the preparation and use of compounds of structure I but should not be understood as limiting the invention as modifications in materials and methods will be apparent to the skilled person. The following examples should not be construed as limiting the scope of this disclosure. Apart from extending the actual life span, these examples show that the correct use of compositions based on compounds of structure (I) can extend the live time of animals, decelerate and in some cases reverse the development of several independent signs of ageing.

EXAMPLES

Figure 1:
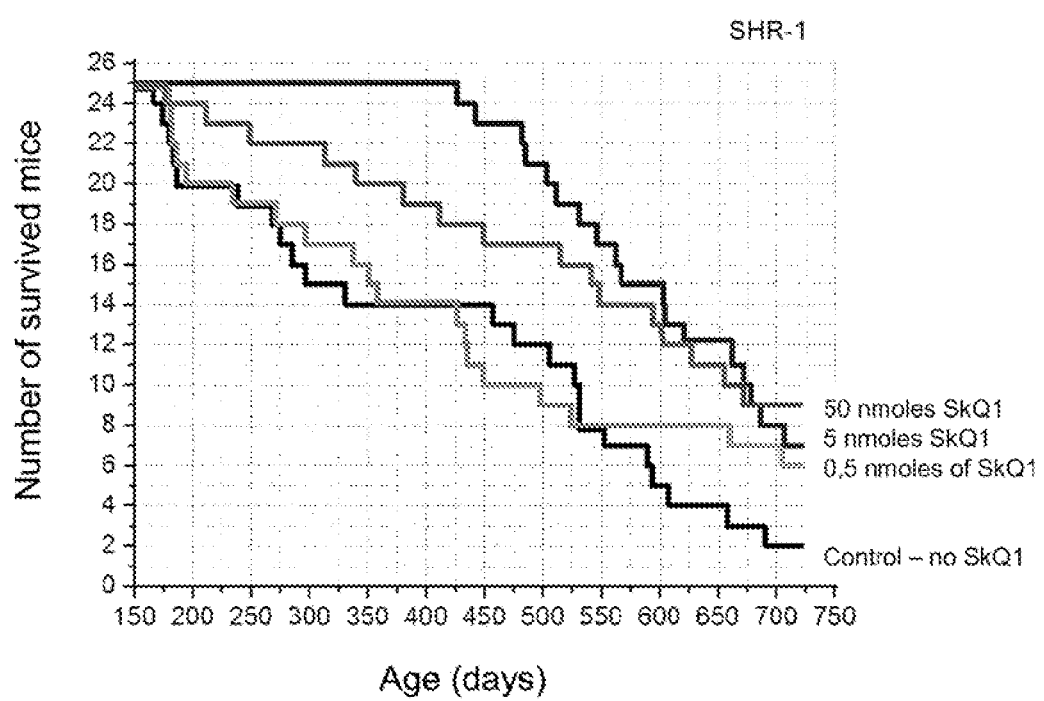
FIG. 1 demonstrates the effect of the preparation on life span of SHR mice. (The figure shows a survival curve for SHR mice daily received SkQ1 with water).

1. Increase of Life Span in SHR Mice by Means of Mitochondria-Targeted SkQ1 Antioxidant An experiment with outbred SHR mice was carried out. The mice were divided into four groups (25 animals per each group). The three groups received a certain amount of SkQ1 with drinking water throughout their lives, and the fourth (control) group received water without SkQ1. Data on the time of animal deaths in all groups are shown in FIG. 1. Dose of SkQ1 is given in nanomoles per kg of animal weight per day.

The data shown in the Figure conclusively demonstrate the ability of SkQ1 to extend the life span of SHR mice which are a generally accepted model for gerontological studies. (V. N. Anisimov, I. N. Alimova, D. A. Baturin, I. G. Popovich, M. A. Zabezhinski, S. V. Rosenfeld, K. G. Manton, A. V. Semenchenko, A. I. Yashin (2003) Dose-dependent effect of melatonin on life span and spontaneous tumor incidence in female SHR mice. Exp Gerontol. 38, 449-461). Indeed, mice that received SkQ1 in optimal doses (1 nanomole per animal per day) revealed much longer life span: in 707 days of the experiment, in the control group, 8% of the animals remained alive, while in the test group—36%, 28% and 24%, respectively.

The same experiment showed that female SHR mice received SkQ1 are characterized by less pronounced age-related changes in estrous function, as compared to the control group. With increasing the duration of the observation period, tendency of decelerating age-related disorders in estrous function in experimental animals becomes more pronounced, which were expressed as increase in the duration of cycle and lowering the frequency of regular cycles. For example, in the $2^{nd}$ cohort in 15-month-old experimental animals received SkQ1 at a dose of 0.01 nanomoles per day, the frequency of regular cycles was 94%, whereas in the control—67%. These data suggest decelerating age-related disorders in estrous function in SHR mice under the influence of SkQ1.

2. Increase of Life Span in Female Fruit Flies (Drosophila melanogaster) by Means of SkQ1

Isogenous laboratory Drosophila line $w^{1118}$ in which all individuals have the same genotype was chosen for the experiments, thus eliminating the influence of genetic differences between individuals on the results of experiments. The mitochondria-targeted antioxidant SkQ1 at a concentration of 1.85 nM was tested. Stock SkQ solution was diluted in distilled water. Adult flies were administered the compound throughout their lives. Since adult flies can feed on food located on the surface, it was decided to spread the SkQ1 solution of a corresponding concentration on the surface of freshly prepared medium poured into test tubes containing the flies.

Virgin females and males of line $w^{1118}$ selected during the day were placed in tubes, each tube contained five individuals (males and females separately), in standard medium. In control tubes, 100 μl of distilled water without SkQ was spread on standard medium surface; in test tubes, 100 μl of the test compound at a selected concentration was spread on standard medium surface. The number of live flies in each tube was recorded daily, once a week flies were transferred to a corresponding fresh medium. All tubes were incubated at 25° C. In each experiment, 100 individuals (20 tubes) were analyzed.

Figure 2:
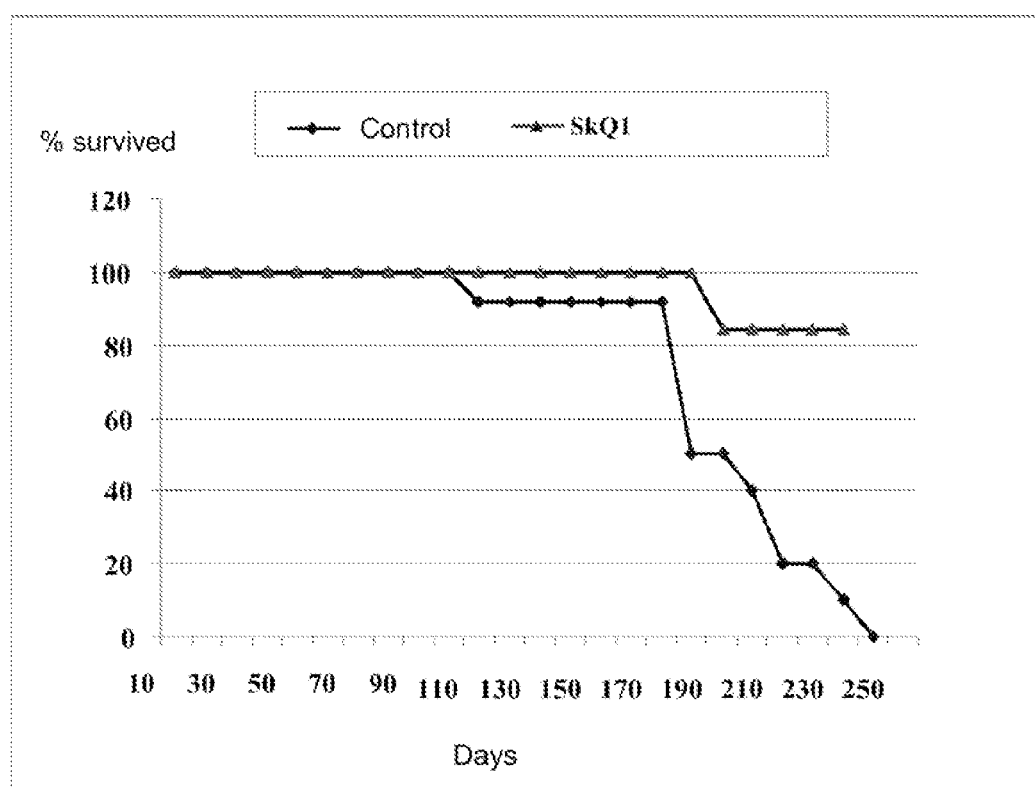
FIG. 2 demonstrates the effect of the preparation on life span of p53 (−/−) transgenic mice lacking the p53 gene. (The figure shows a survival curve for mice lacking the p53 gene daily received SkQ 1 with water).

Analysis of the survival curves for flies showed that SkQ1 at a concentration of 1.85 nM resulted in reliable increase of the average life expectancy from 58 to 66 days (P=0.0012). A fraction of individuals aged 70 days and older in the group received feed with 1.85 nM SkQ1 is reliably higher than that in the control group (0.48 and 0.18, respectively, P=0.0056). The survival curves for flies are shown in FIG. 2.

The results of this experiment indicate that the mitochondrial antioxidant of SkQ1-type increases the life span of flies D. melanogaster.

3. Increase of Life Span in p53 Gene Knockout Mice

Mice lacking the p53 gene (p53−/−) can not synthesize the p53 protein, so-called "guardian of the genome", and can serve as a model of accelerated ageing and death of the organism caused by cancer [for more details, see A. A. Sablina, A. V. Budanov, G. V. Ilyinskaya, L. S. Agapova, J. E. Kravchenko, P. M. Chumakov (2005) The antioxidant function of the p53 tumor suppressor //Nature Med., 11, 1306-1313)]. Within the framework of the aforementioned theory of phenoptosis implying the key role of mitochondrial reactive oxygen species in organism's aging, one may suggest that compounds of structure (I) can significantly extend the life span of p53 (−/−) mice. This example demonstrates the results of such experiment.

Based on the previously conducted PCR analysis detecting p53−/−, p53+/− and p53+/+ mice in the progeny of heterozygous (p53+/−) animals, the two groups of mice were drawn up which received:
  clean drinking water;
  water supplemented with SkQ1 (0.1 nmoles of the preparation per mouse per day (5 nM/kg/day)).

Figure 3:
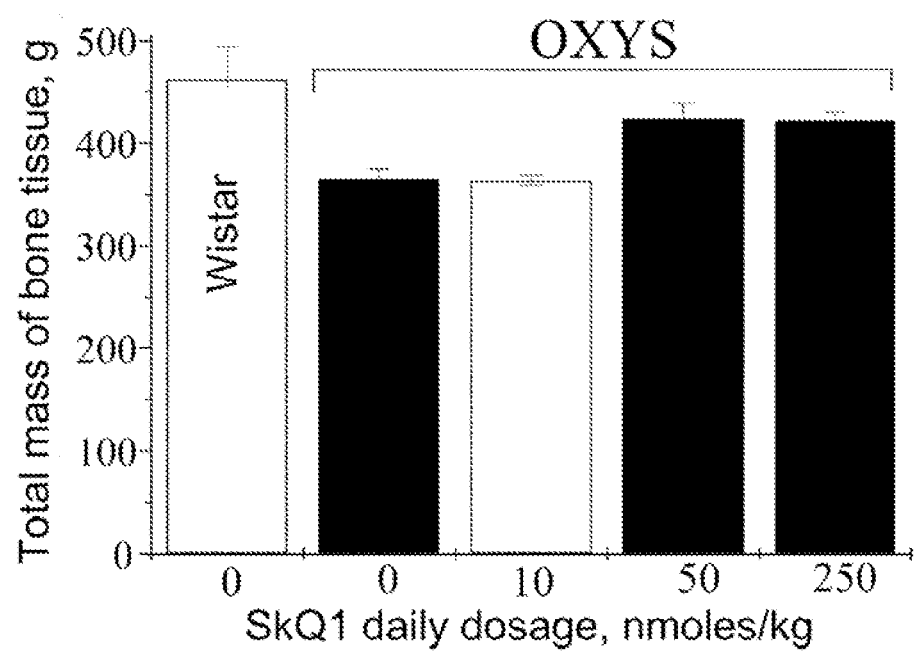
FIG. 3 shows the effect of SkQ1 on the mass of bone tissue of OXYS rats as a result of administering SkQ 1.

The experimental results are shown in FIG. 3.

The experimental curves clearly show a dramatic increase of the life span in animals received SkQ1 with drinking water.

4. Reversing a Sign of Ageing

Senile Blindness in Pets

In support of the possibility of execution of the invention, this experimental example shows several protocols for clinical trials of pharmaceutical compositions based on compounds of structure (I) as a veterinary preparation.

A) Patient—cat, breed—European Shorthair, age—15 years. Diagnosis—retinitis, papillitis, senile generalized progressive retinal dystrophy. Clinical signs—depigmentation of *t. lucidum*, the optic disk (OD) is violet. Retinal detachment. Vision is absent.

Treatment—daily instillation of 250 nM SkQ1 solution (in physiological solution at pH 6.5).

Results—after 10 days of the treatment the pupil began to respond to light, the cat began to play with the ball and see even small objects. In the study of eye fundus, only pinpoint hemorrhages were identified. Retinal detachment and dystrophy areas are absent. OD became pink. After 21 days of the treatment—vision retained; retinal detachment and dystrophy areas are absent. OD is pink.

B) Patient—horse, gelding, not thoroughbred, age—20 years. Diagnosis—senile blindness associated with degeneration of the retina and its vessels. Clinical signs—shortening and thinning of retinal vessels emanating from the optic disk, depigmentation of *t. lucidum t. nigrum*, thinning of the retina over the entire surface of eye fundus. As a result, Choroid blood vessels in the form of straight lines are well visualized, posterior polar senile cataract is detected. The animal cannot see during the last eight months.

Treatment—daily instillation of 250 nM SkQ1 solution (in physiological solution at pH 6.5), and since the $3^{rd}$ month of treatment—2 times a day.

Results after 90 days of the treatment—original color of *t. lucidum* returned, old vessels emanating from OD are filled with blood, highly convoluted, short. OD is pink. The growth of 40 new blood vessels from OD was detected. The vessels are long, filled with blood (similar to foal's vessels). The vision was restored in the animal.

5. Preventing the Development of a Sign of Ageing

Age-Dependent Decrease in Bone Mass (Osteoporosis) in Rats

Osteoporosis is one of the most common senile diseases manifesting itself as bone thinning and increase in bone fragility. Today, this disease has become so commonplace that it can be referred to as a quiet epidemic. In osteoporosis, entire sections of bone tissue disappear, bone loses its complex architecture. Traditional antioxidants are ineffective for osteoporosis prevention (Wolf R. L. et. al. Lack of a relation between vitamin and mineral antioxidants and bone mineral density: results from the Women's Health Initiative //American Journal of Clinical Nutrition, 2005, 82, 3, 581-588). The next series of experiments demonstrates the possibility of preventing the development of the main symptom of osteoporosis—reduced bone mineral density.

Experiments were conducted on the two lines of rats—Wistar and OXYS. Genetically determined metabolic defect, manifesting itself as decreased resistance of OXYS rats towards oxidative stress, leads to changes in their organism which may be regarded as accelerated ageing syndrome. In particular, reduced bone mineral density in OXYS rats, as compared to Wistar rats, is observed. Such changes are also observed in osteoporosis in humans that allows us to consider these animals as an adequate model of senile osteoporosis in humans.

Wistar and OXYS rats,—control rats and those who received two courses of SkQ1 (50 nanomoles per kg of body weight per day), were studied. The animals received the preparation since 1.5 and 4 months of age for 45 days. At the age of 6 months, bone tissue state was studied by X-ray densitometry.

Figure 4:
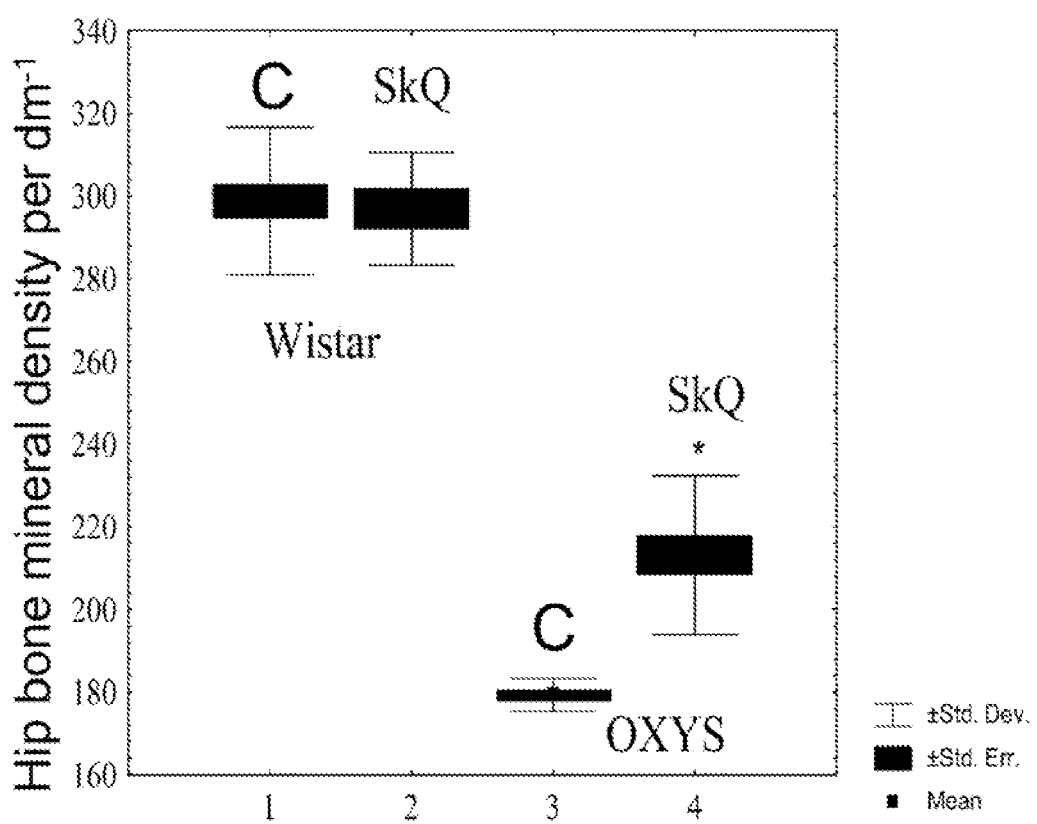
FIG. 4 shows data on the preparation-induced changes in bone mineral density of Wistar and OXYS rats. (The figure shows changes in bone mineral density (hip) as a result of administering SkQ 1).
Figure 5:
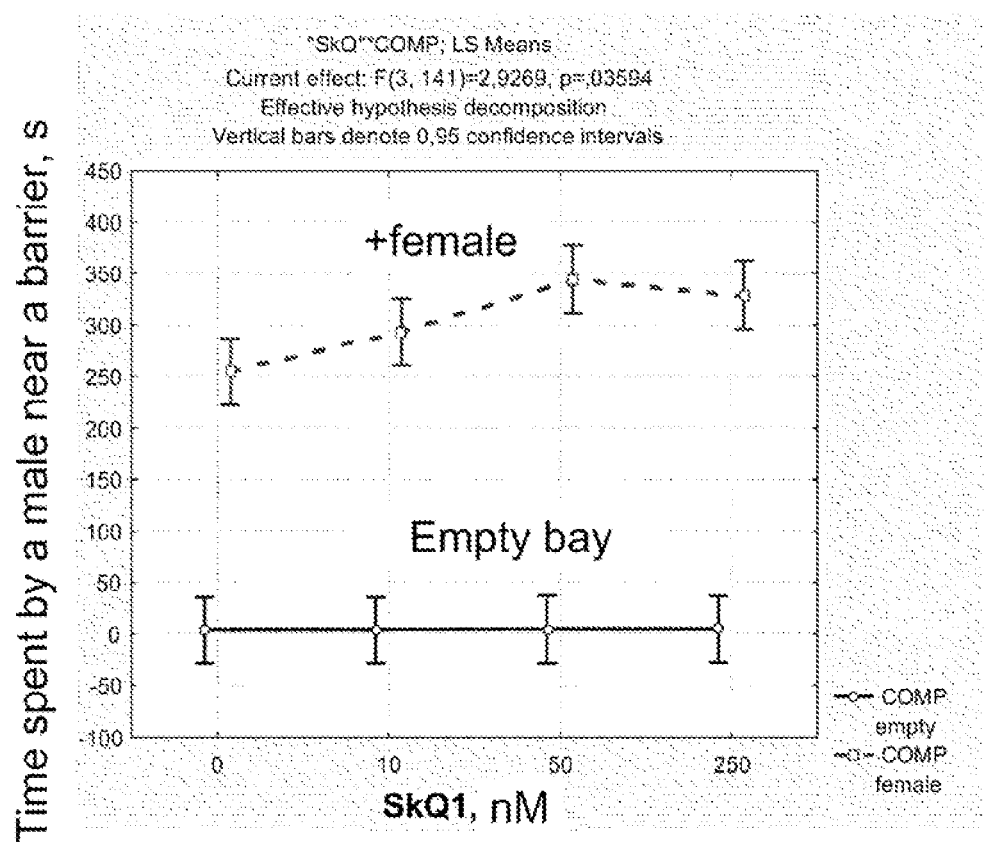
FIG. 5 shows the results of the long-term course of administering the preparation on the extent of sexual motivational behavior in male OXYS rats. (The figure shows the effect of administering SkQ1 on time spent by a male rat near a female rat separated by a barrier inserted between the rats (a parameter characterizing male sexual motivation)).

It was shown that, in OXYS rats, the preparation reliably increased bone mineral density of femur and tibia (FIG. 4) and the total mass of bone tissue (FIG. 5). Thus, the preparation reduces the severity of osteoporosis in OXYS rats.

6. Preventing the Development of a Sign of Ageing

Age-Dependent Reduction of Sexual Motivation in Rats

It is known that ageing in higher organisms is often accompanied by weakening of reproductive instincts and reduced sexual motivation. The next series of experiments demonstrates the possibility of preventing the development of such behavioral disorders with the previously mentioned Wistar and OXYS rats as an example.

Both at the age of 3 months and at one year Wistar males show considerable interest in females. In the study of sexual motivation in OXYS rats at different age periods, somewhat different results were obtained. One year old OXYS males show less interest in females, as compared to OXYS males at the age of 3 months.

The effect of monthly course of SkQ1 (50 nanomoles per day) on the extent of sexual arousal in one year old Wistar and OXYS males was investigated. To do this, an experimental model of sexual arousal was used—males were kept under conditions allowing them to see the receptive female, perceive the female's smell, but excluding physical contact with the female. Under these conditions, male rats and male mice show increase in blood testosterone level and typical motivational behavior.

Figure 6:
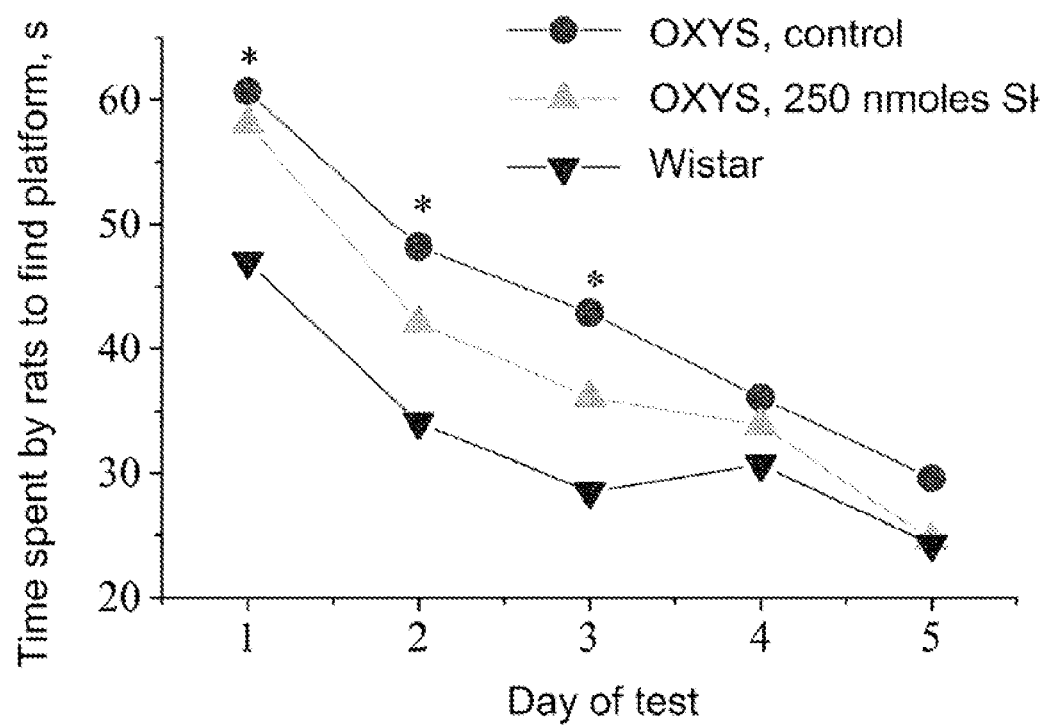
FIG. 6 shows data on a prophylactic effect of SkQ1 on age-related dysfunctions of memory and learning ability (the Morris maze test) in OXYS rats. (The figure shows the effect of administering SkQ1 on time spent by rats to find the platform under water in the Morris maze (test of learning ability)).

It was shown that under the influence of SkQ1, interlinear differences between Wistar and OXYS rats by the main behavioral indicator of sexual arousal,—time spent by a male rat near a female rat separated by a barrier inserted between the rats, disappeared. SkQ1 reliably increased this indicator in OXYS rats administered 50 and 250 nanomoles of SkQ1 (as compared to the values for sexual arousal in the control (no SkQ1 was given) males (FIG. 6). Thus, long-term SkQ1 administration enhanced the sexual motivation of OXYS male rats with a genetic predisposition to premature ageing, bringing it to the level shown by Wistar male rats with a normal rate of ageing.

7. The Effect of Long-Term SkQ1 Administration on "Investigatory Reflex" and the Ability of Animals to Learn The next series of experiments reveals SkQ1 ability to decelerate the development of age-related changes in learning ability, using Wistar and OXYS rats as an example.

The Morris water maze test is actively used for studies on learning and long-term spatial memory in animals. The method of Morris allows to evaluate strategies for behavior, dynamics of skill formation, to detect even weak differences in behavior. This test evaluates the ability of an animal, swimming in the opaque water of the pool and looking at the signs on its sides, to learn how to find the invisible, hidden platform under water, no matter from what point of the perimeter of the pool the animal was released. Progress in passing spatial orientation tests depends on the function of the hippocampus, and, in the development of senile neurodegenerative processes, this function is significantly reduced. Preliminary experiments showed that Wistar rats at the age of 3, 12 and 16 months do not differ in their ability to learn in the Morris maze, whereas in OXYS rats such ability decreases with age.

In subsequent experiments, 4 groups of 16-month-old animals: control Wistar and OXYS rats, and groups received the preparation since 1.5 months at a dose of 250 nanomoles per kg of body weight, were used. A latent period of time spent by rats to find the platform depended only on the genotype—it took longer in OXYS rats than in Wistar rats—OXYS rats coped worse with the task. Under the influence of SkQ1, interlinear differences between Wistar and OXYS rats disappeared—SkQ1 improved the ability of OXYS rats to learn (FIG. 7).

Thus, it was shown that prophylactic administration of the preparation SkQ1 has a positive effect on memory and prevents age-related decline in the ability to learn in the Morris maze in OXYS rats.

A further series of behavioral tests "open field" and "elevated cruciform maze" demonstrated a positive effect of SkQ1 on search and exploratory activity of rats. In addition, a clear stress-protective effect of SkQ1 administration was observed with Wistar rats.

The invention claimed is:

1. A method of reducing age-related changes in estrus function, increasing age-related learning, slowing down the development of osteoporosis, treating age dependent reduction in sexual motivation, or treating a senile blindness selected from retinitis, papillitis, retinal dystrophy and degeneration of retina antis vessels in a mammal, comprising administering to the mammal a therapeutically effective amount of a compound of formula:

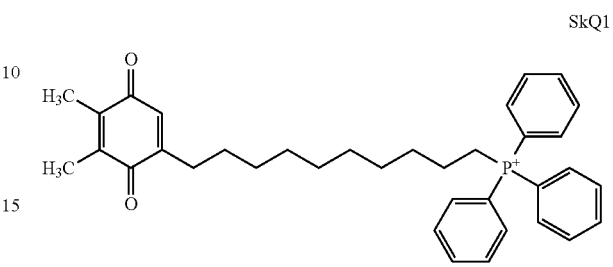

SkQ1 and reduced forms thereof,
a pharmacologically acceptable anion; and
a pharmaceutically acceptable carrier.

2. The method of claim 1, wherein the mammal is human.

3. The method of claim 1, wherein the disorder is osteoporosis.

4. The method of claim 1, wherein the disorder is an age-related dementia.

5. The method of claim 1, wherein another geriatric therapeutic preparation is administered simultaneously, with, before, or after SkQ1 for the treatment of an age-related disease.

6. The method according to claim 1, wherein the effective amount administered is from 0.025 to 120,000 microgram per kg of the mammal for oral administration, and from 0.001 to 10,000 microgram per kg of the mammal for intravenous administration.

7. The method according to claim 4, wherein the age-related dementia is Alzheimer's disease.

* * * * *